(12) United States Patent
Platzek et al.

(10) Patent No.: US 7,083,516 B2
(45) Date of Patent: Aug. 1, 2006

(54) PROCESS FOR THE PRODUCTION OF TRIIODOTRIMESIC ACID

(75) Inventors: Johannes Platzek, Berlin (DE); Ulrich Niedballa, Berlin (DE); Heiko Schirmer, Berlin (DE); Heinz Gries, Berlin (DE)

(73) Assignee: Schering AG, Berlin (DE)

( * ) Notice: Subject to any disclaimer, the term of this patent is extended or adjusted under 35 U.S.C. 154(b) by 19 days.

(21) Appl. No.: 10/890,522

(22) Filed: Jul. 14, 2004

(65) Prior Publication Data

US 2005/0070735 A1    Mar. 31, 2005

Related U.S. Application Data

(60) Provisional application No. 60/488,373, filed on Jul. 18, 2003.

(51) Int. Cl.
*C07C 51/255*    (2006.01)

(52) U.S. Cl. .................................................. 462/409
(58) Field of Classification Search ............... None
See application file for complete search history.

(56) References Cited

U.S. PATENT DOCUMENTS

| 5,047,228 A | * | 9/1991 | Gries et al. ............ 424/9.454 |
| 5,882,628 A |   | 3/1999 | Almen et al. |

FOREIGN PATENT DOCUMENTS

| DE | 1271702 | 2/1963 |

* cited by examiner

*Primary Examiner*—Paul A. Zucker
(74) *Attorney, Agent, or Firm*—Millen, White, Zelano, Branigan, P.C.

(57) ABSTRACT

A new process for the production of triiodotrimesic acid that is used as an intermediate product for the synthesis of x-ray contrast media is described.

5 Claims, No Drawings

PROCESS FOR THE PRODUCTION OF TRIIODOTRIMESIC ACID

This application claims the benefit of the filing date of U.S. Provisional Application Ser. No. 60/488,373 filed Jul. 18, 2003, which is incorporated by reference herein.

Triiodotrimesic acid (formula I) is an important intermediate product for the production of nonionic triiodized x-ray contrast media. Thus, the production of tris-amides of triiodotrimesic acid is described in, for example, DE 3001292 (Schering). Such compounds are especially advantageous because of their advantageous pharmacological properties. Attempts to make economic use of these tris-amides have failed because, up until now, no commercially usable way has been found to access the actual starting compound, the triiodotrimesic acid. Further development of a contrast medium with especially good properties, iosimide, which was already in phase III of the clinical examinations, was unsuccessful due to the high production costs of the triiodotrimesic acid.

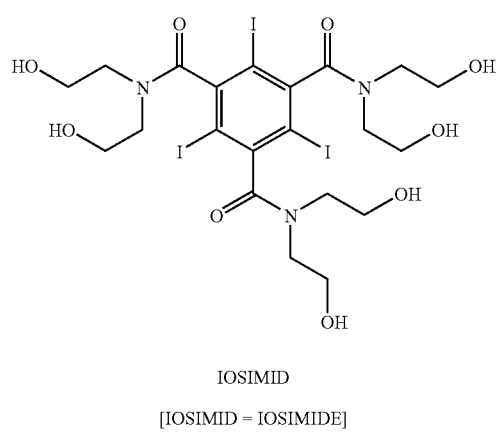

IOSIMID

[IOSIMID = IOSIMIDE]

Thus, in DE 2831496, the production of the triiodotrimesic acid, starting from nitroisophthalic acid, is described:

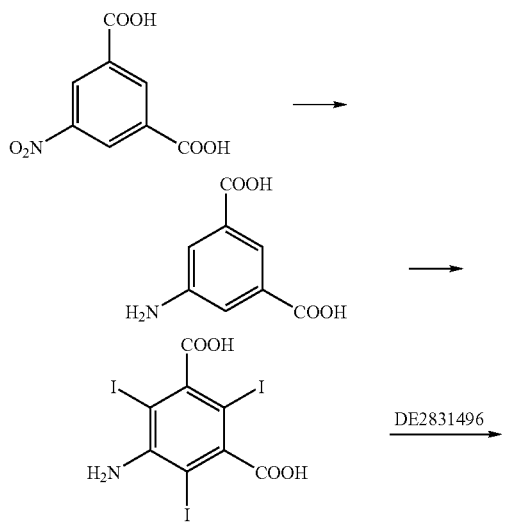

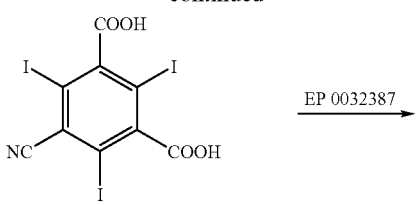

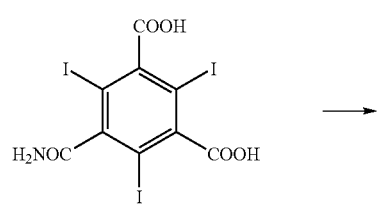

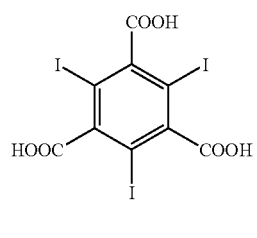

(I)

In this process, nitroisophthalic acid is hydrogenated to form an amino compound and then iodized with chloroiodine. The introduction of the missing carboxyl group can be accomplished with a Sandmeyer reaction ($HNO_2$/KCN/CuCN). This reaction step proved very critical especially in increasing coarseness of the batch, since, on the one hand, hydrogen cyanide is produced, and in addition the copper ions must be used in excess. The removal of copper wastes from the reaction water can be considered especially critical on an industrial scale. A critical step is also the complete saponification of nitrile to carboxylic acid. In this connection, the process has to pass through an intermediate stage, the amide, which proved very difficult to hydrolyze.

In another patent (NYCOMED: U.S. Pat. No. 5,882,628), intermediate stages are described that were considered as starting products for the synthesis of triiodotrimesic acid:

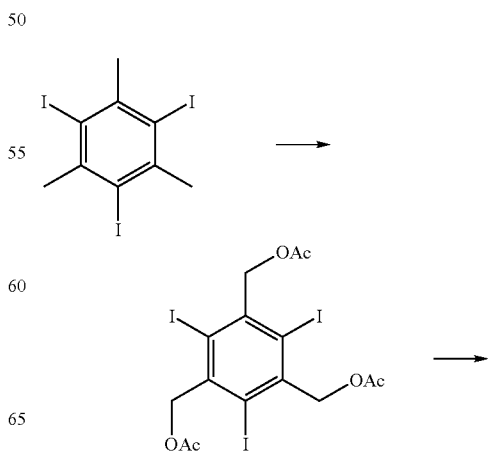

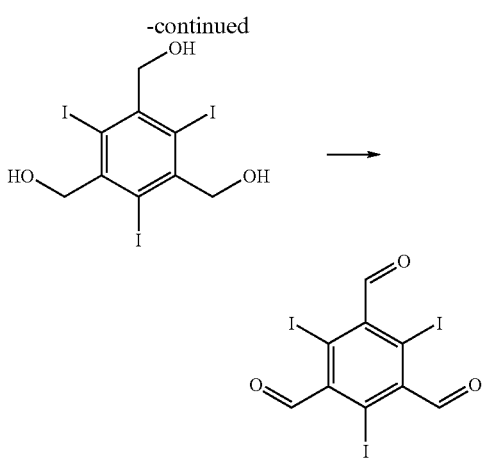

Triiodomesitylene is converted under acetylating conditions in an oxidation reaction with potassium permanganate/acetic anhydride/acetic acid/sulfuric acid into triacetate (yield: 35%). The triacetate is isolated and saponified with potassium carbonate in methanol to tris alcohol (yield: 94%). The tris alcohol is then reacted to form tris aldehyde by Swern oxidation in dimethyl sulfoxide as a solvent in a yield of 67%.

Additional oxidation to tricarboxylic acid was not described in this patent and also is not reported with this step in literature.

There was therefore the need for a process that provides the triiodotrimesic acid in a higher total yield from advantageous environmental and safety standpoints and that also has the capacity for increasing coarseness of the batch. These requirements are, surprisingly enough, met by the new process that is present here. The following synthesis diagram shows the new method of synthesis that starts from triiodomesitylene:

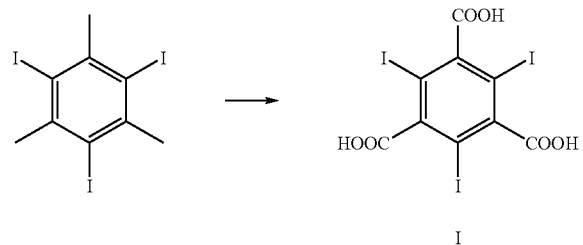

In this connection, starting from triiodomesitylene, the reaction is performed with potassium or sodium permanganate in a mixture that consists of acetic acid anhydride, acetic acid and sulfuric acid in a volume ratio of 15–30: 7–15:0.75–1.25, preferably 20:10:2. The sulfuric acid is used in the concentration of 70%–100%, preferably 95–100%. The reaction is carried out at temperatures of 10 to 120° C., preferably 20–100° C., especially preferably 40–80° C. The reaction period is 18–36 hours, preferably 20–25 hours.

Then, it is distilled off. This can be carried out directly from the batch, whereby the pressure optionally is reduced. In this case, a mixture that consists of acetic acid and acetic anhydride is obtained. Also, however, only water can be added to destroy excess acetic acid anhydride, and then pure acetic acid is distilled off. The recovered acetic acid can be reused.

Then, the sulfuric acid is neutralized in the residue by adding an inorganic base such as sodium hydroxide solution, potassium hydroxide solution, or calcium hydroxide in solid form, or, preferably, as an aqueous solution, and the concentration by evaporation is continued. After concentration by evaporation is completed, water is added at temperatures of between 60–100° C., then it is absorptively precipitated, and the precipitated crude product is filtered off, which is optionally washed with water and used directly in the subsequent reaction without purification or drying.

For this purpose, a suspension of the crude product in an aqueous potassium or sodium permanganate solution is introduced at temperatures of 60–100° C., preferably 80–100° C. (reflux) and mixed with an aqueous solution of an inorganic base, preferably sodium hydroxide solution, potassium hydroxide solution, calcium hydroxide, sodium carbonate or potassium carbonate, but especially preferably NaOH or KOH. The period of dropwise addition of the base is 30 minutes to 10 hours, preferably 30 minutes to 3 hours. Then, it is stirred for 1 to 24 hours, preferably 3–12 hours, especially preferably 4–8 hours, at temperatures of between 60 and 100° C., especially preferably 80–100° C.

The subsequent working-up can be carried out in different ways:

1. Excess oxidizing agent can be destroyed by adding a reducing agent in solid or dissolved form (aqueous solution). For this purpose, in particular inorganic sulfites or hydrogen sulfites, such as sodium sulfite/hydrogen sulfite or potassium sulfite/hydrogen sulfite, especially preferably sodium sulfite or lower alcohols such as methanol, ethanol, isopropanol, and glycol are suitable. The latter takes place at temperatures of between 10 to 100° C., preferably 20–80° C. Then, a pH of 0.1–3, preferably 0.5–1, is set by adding sulfuric acid, and the product is extracted by extraction with an organic solvent, such as ethyl acetate, propyl acetate, methyl-butyl ether (MTB), tetrahydrofuran (THF), n-butanol, methyl-THF, dichloromethane, or toluene. Ethyl acetate and MTB are preferred. The organic phases can optionally be washed with water, brine or acidified water and are evaporated to the dry state. It has proven especially advantageous to redistill the solvent that is used for crystallization directly. In this case, the first solvent is replaced by the second solvent during the distillation by continuous addition of a second solvent. As a solvent for crystallization, especially cyclohexane and n-heptane, as well as their mixtures with ethyl acetate, toluene and MTB, have proven their value.

In many cases, an extraction with an organic solvent, as described above, can also be eliminated. To this end, it is largely evaporated to the dry state under reduced pressure, and then water is largely removed by adding an azeotrope-forming solvent such as methanol, ethanol, isopropanol, dichloromethane, MTB, ethyl acetate, butyl acetate, butanol, toluene or THF. The amount of residual water is determined by Karl-Fischer (KF) titration. Then, the remaining residue is absorptively precipitated with an organic solvent, such as methanol, ethanol, isopropanol, dichloromethane, MTB, ethyl acetate, butyl acetate, butanol, toluene or THF at temperatures of between 20–100° C., and salts are filtered out. The filtrate can be evaporated to the dry state or else, as described above, a solvent that is suitable for crystallization can be redistilled.

2. In many cases, it has proven advantageous not to add any reducing agent but rather to set the pH to 0.1–3, but preferably 0.1–1, by adding sulfuric acid and then to evaporate it to the dry state as described above under reduced pressure and to absorptively precipitate the residue with an organic solvent (analogous procedure to that under 1).

The process that is described here is characterized by several important advantages compared to the process of the prior art:

The inexpensive and nontoxic potassium or sodium permanganate is used as the only active ingredient. The manganese wastes that are produced can be made reusable in a recycling process by further oxidation.

The process is robust and can easily be implemented on a multi-ton scale. It is distinguished by an environmentally sound solvent. The process is inexpensive in implementation, consists of only one stage and provides a high total yield of 75–80% of theory.

This process thus represents a valuable contribution to the production of an intermediate stage of the triiodized trisamides that are important for medical diagnosis.

The examples below are used to described the new process:

Production of Triiodotrimesitylene

Carried out according to Synthesis 6, 486 (1980); WO 96/09282, J. Med. Chem. (2000) 43 (10), 1940 or according to Synlett (2002), (4), 598

Production of Triiodotrimesic Acid in a Single-Pot Process (Variant I)

1 kg (2.01 mol) of triiodomesitylene and 1.27 kg (8.03 mol) of potassium permanganate, suspended in 2.06 l of acetic anhydride, 1.03 l of acetic acid and 206 ml of concentrated sulfuric acid, are stirred for 20 hours at 40° C. After the reaction is completed, 285.8 ml of water is carefully added while being stirred, and stirring is continued for 2 hours at room temperature. Then, 618.3 ml of 50% sodium hydroxide solution (exactly the amount to neutralize the sulfuric acid!) is added. Then, it is largely distilled off (concentrated by evaporation) under reduced pressure. While being stirred, 10 l of water is added in drops and then stirred for one hour at 10° C. The deposited precipitate is added to a solution that consists of 2.54 kg (16.07 mol) of potassium permanganate in 10 l of water, and it is heated to 80° C. 100 ml of 20% sodium hydroxide solution is carefully added in drops to this solution within 30 minutes, and it is then refluxed for 6 hours. It is cooled to room temperature (RT), and a concentrated solution of sodium sulfite is added. Then, 50% sulfuric acid is added in drops up to a pH of 6, and it is stirred for one hour at room temperature. Then, the pH is set at 1 with 50% sulfuric acid. 4 l of ethyl acetate is added, and it is stirred thoroughly. The organic phase is separated, and the aqueous phase is extracted two more times with 1 l of ethyl acetate. The organic phases are combined, rewashed once with 5 l of water and then redistilled with cyclohexane. During cooling (0° C.), the product crystallizes out.

Yield: 0.886 kg (75% of theory) Elementary analysis:

| Cld.: | C 18.39 | H 0.51 | J 64.77 |
|---|---|---|---|
| Fnd.: | C 18.48 | H 0.60 | J 64.69 |

Production of Triiodotrimesic Acid in a Single-Pot Process (Variant II)

1 kg (2.01 mol) of triiodomesitylene and 1.27 kg (8.03 mol) of potassium permanganate, suspended in 3.02 l of acetic anhydride, 1.55 l of acetic acid and 309 ml of concentrated sulfuric acid, are stirred for 22 hours at 45° C. After the reaction is completed, 285.8 ml of water is carefully added while being stirred, and stirring is continued for 2 hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and it is then stirred for one hour at 10° C. The deposited precipitate is added to a solution that consists of 2.54 kg (16.07 mol) of potassium permanganate in 10 l of water, and it is heated to 90° C. 100 ml of 20% sodium hydroxide solution is carefully added to this solution within one hour, and it is then refluxed for 7 hours. It is cooled to room temperature, and a concentrated solution of sodium sulfite is added. Then, 50% sulfuric acid is added in drops up to a pH of 6, and it is stirred for one hour at room temperature. Then, a pH of 1 is set with 50% sulfuric acid. 4 l of ethyl acetate is added, and it is stirred thoroughly. The organic phase is separated, and the aqueous phase is extracted two more times with 1 l of ethyl acetate. The organic phases are combined and rewashed once with 5 l of water. The ethyl acetate solution is distilled off to remove azeotropic water (water content according to Karl-Fischer titration <0.2%). A thus produced solution can be used for further reaction (e.g., production of the acid chloride with $SOCl_2$). The yield was determined by concentration by evaporation of an aliquot.

Yield: 0.945 kg (80% of theory) Elementary analysis:

| Cld.: | C 18.39 | H 0.51 | J 64.77 |
|---|---|---|---|
| Fnd.: | C 18.51 | H 0.64 | J 64.58 |

Production of Triiodotrimesic Acid in a Single-Pot Process (Variant III)

1 kg (2.01 mol) of triiodomesitylene and 1.27 kg (8.03 mol) of potassium permanganate, suspended in 2.47 lof acetic anhydride, 1.24 l of acetic acid and 247 ml of concentrated sulfuric acid, are stirred for 24 hours at 50° C. After the reaction is completed, 285.8 ml of water is carefully added while being stirred, and stirring is continued for 2 hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and then it is stirred for one hour at 10° C. The deposited precipitate is added to a solution that consists of 2.54 kg (16.07 mol) of potassium permanganate in 10 l of water, and it is heated to 85° C. 100 ml of 20% sodium hydroxide solution is carefully added in drops to this solution within 2 hours, and it is then refluxed for 8 hours. It is cooled to room temperature, and a concentrated solution that consists of sodium sulfite is added. Then, 50% sulfuric acid is added in drops up to a pH of 6, and it is stirred for one hour at room temperature. Then, a pH of 1 is set with 50% sulfuric acid. It is largely concentrated by evaporation in a vacuum, and residual water is azeotropically distilled off by adding isopropanol. The isopropanol is added continuously.

At a water content <1% (KF), another 10 l of isopropanol is added, and it is stirred for one hour at 40° C. Filtration is done from salt paste, and it is flushed two more times with 3 l of isopropanol. The filtrate is evaporated to the dry state in a vacuum.

Yield: 0.909 kg (77% of theory) Elementary analysis:

| Cld.: | C 18.39 | H 0.51 | J 64.77 |
|---|---|---|---|
| Fnd.: | C 18.27 | H 0.59 | J 64.85 |

Production of Triiodotrimesic Acid in a Single-Pot Process (Variant IV)

1 kg (2.01 mol) of triiodomesitylene and 1.27 kg (8.03 mol) of potassium permanganate, suspended in 3.30 l of acetic anhydride, 1.65 l of acetic acid and 330 ml of concentrated sulfuric acid, are stirred for 30 hours at 50° C. After the reaction is completed, 285.8 ml of water is carefully added while being stirred, and stirring is continued for 2 hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and it is then stirred for one hour at 10° C. The deposited precipitate is added to a solution that consists of 2.54 kg (16.07 mol) of potassium permanganate in 10 l of water, and it is heated to 70° C. Within 3 hours, 100 ml of 20% sodium hydroxide solution is carefully added in drops to this solution, and it is then refluxed for 6 hours. It is cooled to room temperature, and a concentrated solution that consists of sodium sulfite is added. Then, 50% sulfuric acid is added in drops up to a pH of 6, and it is stirred for one hour at room temperature. Then, the pH is set at 1 with 50% sulfuric acid. It is largely concentrated by evaporation in a vacuum, and residual water is azeotropically distilled out by adding ethanol (continuous addition of ethanol). At a water content <1% (KF), another 10 l of ethanol is added, and it is stirred for one hour at 40° C. Filtration is done from salt paste, and it is flushed two more times with 5 l of isopropanol. The filtrate is evaporated to the dry state in a vacuum.

Yield: 0.921 kg (78% of theory) Elementary analysis:

| Cld.: | C 18.39 | H 0.51 | J 64.77 |
|---|---|---|---|
| Fnd.: | C 18.31 | H 0.55 | J 64.56 |

Production of Triiodotrimesic Acid in a Single-Pot Process (Variant V)

1 kg (2.01 mol) of triiodomesitylene and 1.27 kg (8.03 mol) of potassium permanganate, suspended in 2.88 l of acetic anhydride, 1.44 l of acetic acid and 288 ml of concentrated sulfuric acid, are stirred for 24 hours at 45° C. After the reaction is completed, 285.8 ml of water is carefully added while being stirred, and stirring is continued for 2 hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and it is then stirred for one hour at 10° C. The deposited precipitate is filtered off, and it is rewashed once with 10 l of water. The precipitate is added to a solution that consists of 2.54 kg (16.07 mol) of potassium permanganate in 10 l of water, and it is heated to 75° C. 100 ml of 20% sodium hydroxide solution is added in drops to this solution within 45 minutes, and then it is refluxed for 7 hours. It is cooled to room temperature, and a pH of 1 is set by adding 50% sulfuric acid. It is largely concentrated by evaporation in a vacuum, and residual water is azeotropically distilled out by adding isopropanol (continuous addition of isopropanol). At a water content <1% (KF), another 10 l of isopropanol is added, and it is stirred for one hour at 40° C. Filtration is done from salt paste, and it is flushed two more times with 5 l of isopropanol. The filtrate is evaporated to the dry state in a vacuum.

Yield: 0.897 kg (76% of theory) Elementary analysis:

| Cld.: | C 18.39 | H 0.51 | J 64.77 |
|---|---|---|---|
| Fnd.: | C 18.48 | H 0.56 | J 64.84 |

Production of Triiodotrimesic Acid in a Single-Pot Process (Variant VI)

1 kg (2.01) of triiodomesitylene and 1.27 kg (8.03 mol) of potassium permanganate, suspended in 2.68 l of acetic anhydride, 1.34 l of acetic acid and 268 ml of concentrated sulfuric acid, are stirred for 20 hours at 55° C. After the reaction is completed, 285.8 ml of water is carefully added while being stirred, and it is stirred for two more hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and it is then stirred for one hour at 10° C. The deposited precipitate is filtered off, and it is rewashed once with 10 l of water. The precipitate is added to a solution that consists of 2.54 kg (16.07 mol) of potassium permanganate in 10 l of water, and it is heated to 80° C. 100 ml of 20% sodium hydroxide solution is carefully added in drops to this solution within one hour, and it is then refluxed for 10 hours. It is cooled to room temperature, and a pH of 1 is set by adding 50% sulfuric acid. It is largely concentrated by evaporation in a vacuum, and residual water is azeotropically distilled off by adding ethanol (continuous addition of ethanol). At a water content <1% (KF titration), another 10 l of ethanol is added, and it is stirred for one hour at 40° C. Filtration is done from salt paste, and it is flushed two more times with 5 l of ethanol. The filtrate is evaporated to the dry state in a vacuum.

Yield: 0.886 kg (75% of theory) Elementary analysis:

| Cld.: | C 18.39 | H 0.51 | J 64.77 |
|---|---|---|---|
| Fnd.: | C 18.45 | H 0.60 | J 64.59 |

Production of Triiodotrimesic Acid in a Single-Pot Process (Variant VII)

1 kg (2.01) of triiodomesitylene and 1.27 kg (8.03 mol) of potassium permanganate, suspended in 2.27 l of acetic andydride, 1.13 l of acetic acid and 227 ml of concentrated sulfuric acid, are stirred for 22 hours at 40° C. After the reaction is completed, 285.8 ml of water is carefully added while being stirred, and stirring is continued for two hours at room temperature. Then, 618.3 ml of 50% sodium hydroxide solution (exactly the amount to neutralize the sulfuric acid!) is added. Then, it is largely distilled off (concentrated by evaporation) under reduced pressure. 10 l of water is added in drops while being stirred, and then it is stirred for one hour at 10° C. The deposited precipitate is filtered off, and it is rewashed once with 10 l of water. The precipitate is added to a solution that consists of 2.54 kg (16.07 mol) of potassium permanganate in 10 l of water, and it is heated to 90° C. 100 ml of 20% sodium hydroxide solution is carefully added in drops to this solution within 30 minutes, and then it is refluxed for 7 hours. It is cooled to room temperature, and a pH of 1 is set by adding 50% sulfuric acid. It is largely concentrated by evaporation in a vacuum, and residual water is azeotropically distilled out by adding methanol (continuous addition of methanol). At a water content <2% (KF titration), another 10 l of methanol is added, and it is stirred for one hour at 40° C. Filtration is done from salt paste, and it is flushed two more times with 5 l of methanol. The filtrate is evaporated to the dry state in a vacuum.

Yield: 0.897 kg (76% of theory) Elementary analysis:

| Cld.: | C 18.39 | H 0.51 | J 64.77 |
| Fnd.: | C 18.33 | H 0.62 | J 64.80 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 103 32 574.3, filed Jul. 14, 2003, and U.S. Provisional Application Ser. No. 60/488,373, filed Jul. 18, 2003, are incorporated by reference herein.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Process for the production of triiodotrimesic acid, characterized in that in an oxidation process, triiodomesitylene is reacted with potassium or sodium permanganate in a mixture that consists of acetic acid anhydride, acetic acid and sulfuric acid at temperatures of 10 to 120° C. within 18 to 36 hours, and then the thus obtained crude product is treated for one to 24 hours with an aqueous potassium or sodium permanganate solution at temperatures of 60 to 100° C. in the presence of an aqueous inorganic base.

2. Process according to claim 1, wherein the reaction is carried out at 40 to 80° C.

3. Process according to claim 1, wherein the reaction is performed within 2000 to 25 hours.

4. Process according to claim 1, wherein the basic crude product treatment is performed at 80 to 100° C.

5. Process according to claim 1, wherein the basic crude product treatment is performed within 4 to 8 hours.

* * * * *

UNITED STATES PATENT AND TRADEMARK OFFICE
CERTIFICATE OF CORRECTION

PATENT NO. : 7,083,516 B2
APPLICATION NO. : 10/890522
DATED : August 1, 2006
INVENTOR(S) : Johannes Platzek It is certified that error appears in the above-identified patent and that said Letters Patent is hereby corrected as shown below:

On Title Page, Foreign Application Priority Data: should read -- Jul. 14, 2003 (DE) 103 32 574 --
Column 10, line 16, reads "Process for the production of" should read -- A process for preparing --
Column 10, line 17, reads "characterized in that in" should read -- comprising reacting in --
Column 10, line 18, reads "is reacted with" should read -- with --
Column 10, line 20, reads "temperatures" should read -- a temperature --
Column 10, line 21, reads "then the thus obtained" should read -- then treating the obtained --
Column 10, line 21, reads "product is" should read -- product --
Column 10, line 22, reads "treated for" should read -- for --
Column 10, line 23, reads "temperatures" should read -- a temperature --
Column 10, line 25, reads "Process" should read -- A process --
Column 10, line 26, reads "2000 to 25" should read -- 20 to 25 --
Column 10, line 27, reads "Process" should read -- A process --
Column 10, line 29, reads "Process" should read -- A process --
Column 10, line 31, reads "Process" should read -- A process --

Signed and Sealed this

Sixth Day of March, 2007

JON W. DUDAS
*Director of the United States Patent and Trademark Office*